US012447017B2

(12) United States Patent
Alkhatib

(10) Patent No.: US 12,447,017 B2
(45) Date of Patent: Oct. 21, 2025

(54) DELIVERY SYSTEM RADIOPAQUE (RO) MARKERS FOR TAVR COMMISSURE ALIGNMENT

(71) Applicant: St. Jude Medical, Cardiology Division, Inc., St. Paul, MN (US)

(72) Inventor: Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 896 days.

(21) Appl. No.: 17/691,689

(22) Filed: Mar. 10, 2022

(65) Prior Publication Data

US 2022/0287837 A1 Sep. 15, 2022

Related U.S. Application Data

(60) Provisional application No. 63/159,570, filed on Mar. 11, 2021.

(51) Int. Cl.

| | |
|---|---|
| ***A61F 2/24*** | (2006.01) |
| *A61F 2/95* | (2013.01) |
| *A61M 25/01* | (2006.01) |

(52) U.S. Cl.

CPC .......... *A61F 2/2436* (2013.01); *A61F 2/9517* (2020.05); *A61M 25/0108* (2013.01)

(58) Field of Classification Search

CPC .... A61F 2/2436; A61F 2/9517; A61F 2/2427; A61F 2/2466; A61M 25/0108; A61M 2039/0045

See application file for complete search history.

(56) References Cited

U.S. PATENT DOCUMENTS

| | | | |
|---|---|---|---|
| 3,657,744 | A | 4/1972 | Ersek |
| 4,423,730 | A | 1/1984 | Gabbay |

(Continued)

FOREIGN PATENT DOCUMENTS

| | | | |
|---|---|---|---|
| DE | 102005003632 | A1 | 8/2006 |
| EP | 1129744 | A1 | 9/2001 |

(Continued)

OTHER PUBLICATIONS

Partial International Search Report including Provisional Opinion for Application No. PCT/US2020/038320, mailed Oct. 12, 2020, pp. 1-12.

(Continued)

*Primary Examiner* — Jerrah Edwards
*Assistant Examiner* — Kia Xiong White
(74) *Attorney, Agent, or Firm* — SLEMAN & LUND LLP

(57) ABSTRACT

A catheter assembly for retaining a prosthetic valve as the prosthetic valve is guided to a point of delivery within a patient is provided with radioscopic markers. The markers are distributed within the catheter assembly such that an observer may discern a rotational orientation of the assembly from a radioscopic image of the assembly within the patient. Delivery of the prosthetic valve may include aligning the markers with the commissures of the prosthetic valve and radioscopic observation of the location or movement of the markers to rotationally align the prosthetic valve with a native valve within the patient, such as by aligning the commissures of the prosthetic valve with the commissures of the native valve.

16 Claims, 6 Drawing Sheets

(56) References Cited

U.S. PATENT DOCUMENTS

| | | | |
|---|---|---|---|
| 5,078,720 | A | 1/1992 | Burton et al. |
| 5,415,664 | A | 5/1995 | Pinchuk |
| 5,484,444 | A | 1/1996 | Braunschweiler et al. |
| 5,702,418 | A | 12/1997 | Ravenscroft |
| 5,824,041 | A | 10/1998 | Lenker et al. |
| 5,843,167 | A | 12/1998 | Dwyer et al. |
| 5,924,424 | A | 7/1999 | Stevens et al. |
| 5,968,068 | A | 10/1999 | Dehdashtian et al. |
| 5,980,533 | A | 11/1999 | Holman |
| 6,077,297 | A | 6/2000 | Robinson et al. |
| 6,269,819 | B1 | 8/2001 | Oz et al. |
| 6,306,141 | B1 | 10/2001 | Jervis |
| 6,391,050 | B1 | 5/2002 | Broome |
| 6,468,299 | B2 | 10/2002 | Stack et al. |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,840,663 | B2 | 9/2014 | Salahieh et al. |
| 9,039,759 | B2 | 5/2015 | Alkhatib et al. |
| 11,020,230 | B2 * | 6/2021 | Vola ...................... A61F 2/2466 |
| 2002/0120322 | A1 * | 8/2002 | Thompson .............. A61F 2/915 623/1.11 |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 * | 3/2007 | Bourang ............... A61F 2/2451 623/2.11 |
| 2007/0088431 | A1 | 4/2007 | Bourang et al. |
| 2007/0093781 | A1 | 4/2007 | Kugler et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0224678 | A1 | 9/2011 | Gabbay |
| 2015/0290432 | A1 | 10/2015 | Mathews et al. |
| 2017/0265938 | A1 | 9/2017 | Spence et al. |
| 2018/0207399 | A1 * | 7/2018 | Chou ......................... A61F 2/95 |
| 2018/0243046 | A1 * | 8/2018 | Scott ...................... A61B 1/018 |
| 2018/0280052 | A1 | 10/2018 | Mustapha |
| 2019/0240011 | A1 * | 8/2019 | Fitterer ................. A61F 2/2439 |

FOREIGN PATENT DOCUMENTS

| | | | |
|---|---|---|---|
| EP | 1157673 | A2 | 11/2001 |
| EP | 1 926 455 | A2 | 6/2008 |
| EP | 2061546 | A2 | 5/2009 |
| WO | 02067782 | A2 | 9/2002 |
| WO | 03089039 | A1 | 10/2003 |
| WO | 2007071436 | A2 | 6/2007 |
| WO | 2008030737 | A2 | 3/2008 |
| WO | 08070797 | A2 | 6/2008 |
| WO | 10051025 | A1 | 5/2010 |
| WO | 10087975 | A1 | 8/2010 |

OTHER PUBLICATIONS

Quaden, Rene et al., "Percutaneous Aortic Valve Replacement: Resection Before Implantation", European J. of Cardio-Thoracic Surgery, vol. 27, No. 5, May 2005, pp. 836-840.

Ruiz, Carlos, Overview of PRE-CE Mark Transcatheter Aortic Valve Technologies, Euro PCR, PowerPoint Presentation dated May 25, 2010.

* cited by examiner

DELIVERY SYSTEM RADIOPAQUE (RO) MARKERS FOR TAVR COMMISSURE ALIGNMENT

CROSS-REFERENCE TO RELATED APPLICATION

The present application claims the benefit of the filing date of U.S. Provisional Patent Application No. 63/159,570 filed Mar. 11, 2021, the disclosure of which is hereby incorporated herein by reference.

BACKGROUND

Heart failure is defined as the inability of the heart to pump enough blood to sustain normal bodily functions. Heart failure may be associated with a mechanical failure of a native valve. Such failures may arise because of congenital defects or as a result of age-related changes, infections, or other conditions.

Mechanical failures of the heart may result from a valve disorder. The heart has four valves: the tricuspid, pulmonary, mitral, and aortic valves. These valves have tissue leaflets that open and close with each heartbeat. The leaflets ensure proper blood flow through the four chambers of the heart and to the rest of the body. The heart valves sometimes have the following types of disorders: regurgitation, stenosis, and atresia.

Regurgitation (backflow through or around a valve) often occurs when the valve does not close tightly enough, thereby resulting in blood leaking back into the chambers of the heart rather than flowing forward through the heart or into arteries. Regurgitation often occurs because of prolapse, i.e., when the cusps or leaflets of the valve bulge back into an upper heart chamber during diastole. Stenosis occurs when the cusps or leaflets of a valve stiffen or fuse together, such as from calcification, thereby preventing the valve from fully opening and inhibiting sufficient blood flow through the valve. Atresia occurs when a heart valve lacks an opening for blood to pass through.

Heart valve repair or replacement surgery restores or replaces a defective heart valve. The implantation of prosthetic cardiac valves has become increasingly common. One such procedure, known as Transcatheter Aortic Valve Implantation (TAVI) or Transcatheter Aortic Valve Replacement (TAVR), uses a prosthetic valve mounted on a stent that displaces the diseased native aortic valve. The prosthetic valve is delivered by compressing it to approximately the width of a pencil and introducing it through a variety of access approaches including a transfemoral, transapical, transaortic, subclavian, or radial approach. Using ultrasound and X-ray guidance, the device is positioned and deployed at the level of the native aortic annulus. As the device expands, it is anchored onto and displaces the diseased native valve to restore normal blood flow.

The replacement or repair of the aortic valve with a prosthetic device presents several challenges, including assessing the size and shape of the aortic annulus prior to implantation of the prosthetic device. Selecting an appropriately sized and shaped prosthetic device may pose several challenges because different techniques for measuring the aortic annulus may provide different measurements and measuring during systole or diastole may also have implications for sizing.

Even when an appropriately sized and shaped prosthetic device is selected, precise placement of the device is challenging. Since valves are often made from material that is not radiopaque, such as tissue or fabric, radiologic imaging techniques do not provide a direct way of determining the location of important regions of the valve. The stent typically is metallic and can be visualized in an x-ray image such as a fluoroscopic image. However, even if a clinician possesses a high degree of knowledge as to the construction of the valve assembly, e.g., the placement of the valve with respect to the stent, various regions of the valve assembly may appear to be the same or substantially the same when viewed using radiologic imaging techniques. Due to these challenges, the clinician often finds it difficult to guide the valve to the desired position relative to the patient's vasculature.

Appropriate placement and fit of the valve with respect to a patient's vasculature is important in ensuring proper functioning of the device. An improper fit or placement of the device may result in incomplete apposition or contact with the native aortic annulus, which may cause complications such as perivalvular leakage.

Therefore, a continuing need exists for devices and methods that facilitate the proper placement of prosthetic valves during valve repair or replacement surgery by more accurately and easily determining the location of components of the valve assembly with respect to anatomical landmarks.

BRIEF SUMMARY

The present disclosure generally relates to devices and methods for facilitating proper placement of a medical prosthesis relative to a patient's anatomical structures. More particularly, the present disclosure relates to a delivery device including markers that facilitate placement of the medical prosthesis relative to the patient's anatomical structures.

According to an aspect of the disclosure, the delivery system may include a catheter assembly for retaining a prosthetic valve prior to deployment of the prosthetic valve within the patient, the catheter assembly being marked with one or more radioscopically conspicuous markers. The marker or markers may be radially offset from a central axis of the catheter assembly, and may be located and shaped such that, for any radioscopic view of the catheter assembly from a perspective perpendicular to the central axis, an observer may be able to determine which single rotational position about the central axis or which of two rotational positions about the central axis the catheter assembly may be in. The marker or markers may be angularly aligned with commissures of the prosthetic valve held within the catheter assembly. The catheter assembly may include a sheath and a distal nosecone, and the marker or markers may be embedded within the sheath, the distal nosecone, a shaft of the delivery system, any other distal components of the delivery system, or any combination thereof.

In another aspect, a prosthetic valve delivery system may comprise a catheter assembly having a central axis, the catheter assembly being adapted to retain a prosthetic valve in a collapsed state, and a marker integrated with the catheter assembly at a marker location radially offset from the central axis. The marker may have a contrasting radiopacity to the radiopacity of the material of the catheter assembly on both sides of the marker location in the circumferential direction.

In another aspect, a method of delivering a prosthetic valve into a patient using the system according to any of the foregoing arrangements may comprise making visual reference to the marker within a radioscopic image of the patient while rotating the catheter assembly to a delivery orientation in which the marker is angularly aligned with a commissure of the native valve and while the prosthetic valve is disposed within the catheter assembly such that a commissure attachment feature of the prosthetic valve is angularly aligned with the marker relative to the central axis. The method may also comprise deploying the prosthetic valve while the catheter assembly is in the delivery orientation.

In another aspect, a prosthetic valve delivery system may comprise a catheter assembly having a central axis, the catheter assembly being adapted to retain a prosthetic valve in a collapsed state, the catheter assembly being radioscopically marked such that, for any radioscopic image of the catheter assembly obtained from a perspective orthogonal to the central axis, an observer could conclude that the catheter is in one of at most six unique rotational positions of the catheter assembly about the central axis.

In another aspect, a prosthetic valve delivery system may comprise a catheter assembly having a central axis, the catheter assembly being adapted to retain a prosthetic valve in a collapsed state. The system may also comprise a plurality of markers integrated with the catheter assembly at respective marker locations radially offset from the central axis by an equal offset distance, each marker location being circumferentially aligned with and angularly equidistant from one another relative to the central axis, the markers having a contrasting radiopacity to the material of the catheter assembly on both sides of the marker location in the circumferential direction.

In further arrangements according to any of the foregoing examples, the marker or markers may each be a design feature, structure, element, or a component that is constructed from radiopaque materials or a void created by removing material in a specific desired shape or geometry in one or more of any radiopaque components or structures of the sheath. In yet further arrangements according to any of the foregoing examples, the marker or markers may each be a combination of both added structures or subtracted materials from existing structures on the same sheath catheter. In yet further arrangements according to any of the foregoing examples, the marker or markers may be raised, as in protruding radially from the external surface of the sheath, or the marker or markers may be recessed or flush with the external surface of the sheath.

In yet further arrangements according to any of the foregoing examples, the marker or markers may be placed on the sheath to aid in specific desired placement of the prosthetic heart valve in a desired orientation relative to the patient's anatomy. For example, the marker or markers may be distributed in a manner specific to a specific type of prosthetic valve, a specific type of replacement procedure, or a combination thereof, or in a manner specific to an individual patient, such that the intended orientation of the sheath and prosthetic valve would be immediately apparent in radioscopic images. Such markers may be placed to align with specific features of the patient's anatomy.

BRIEF DESCRIPTION OF THE DRAWINGS

Various embodiments of the present disclosure are described herein with reference to the accompanying drawings, wherein.

DETAILED DESCRIPTION

As used herein in connection with a prosthetic heart valve, the term "inflow end" refers to the end of the heart valve through which blood enters when the heart valve is functioning as intended, and the term "outflow end" refers to the end of the heart valve through which blood exits when the heart valve is functioning as intended. As used herein in connection with a prosthetic heart valve, the term "proximal" refers to the inflow end of the heart valve or to elements of the heart valve that are relatively close to the inflow end, and the term "distal" refers to the outflow end of the heart valve or to elements of the heart valve that are relatively close to the outflow end. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user. As used herein, the terms "substantially," "generally," "approximately," and "about" are intended to mean that slight deviations from absolute are included within the scope of the term so modified. Although the various features of the prosthetic heart valve recited herein are described in connection with a valve for replacing the function of a native aortic valve, it will be appreciated that these features may also be applied to valves for replacing the function of other cardiac valves, including the mitral valve, tricuspid valve, and pulmonary valve.

The present disclosure relates to aspects of delivery systems that may be generally similar to, with features of the present disclosure being among some possible exceptions, that described in U.S. Pat. No. 10,441,418 or U.S. Patent Pub. No. US2020/0397577, the entirety of which are hereby incorporated by reference herein. The prosthetic valve delivered by these systems may be generally similar to, with distinctions mentioned in the present disclosure being among some possible exceptions, that described in U.S. Pat. No. 10,639,148 B2 or U.S. Pat. No. 9,039,759, the entirety of which are hereby incorporated by reference herein.

Figure 1A:
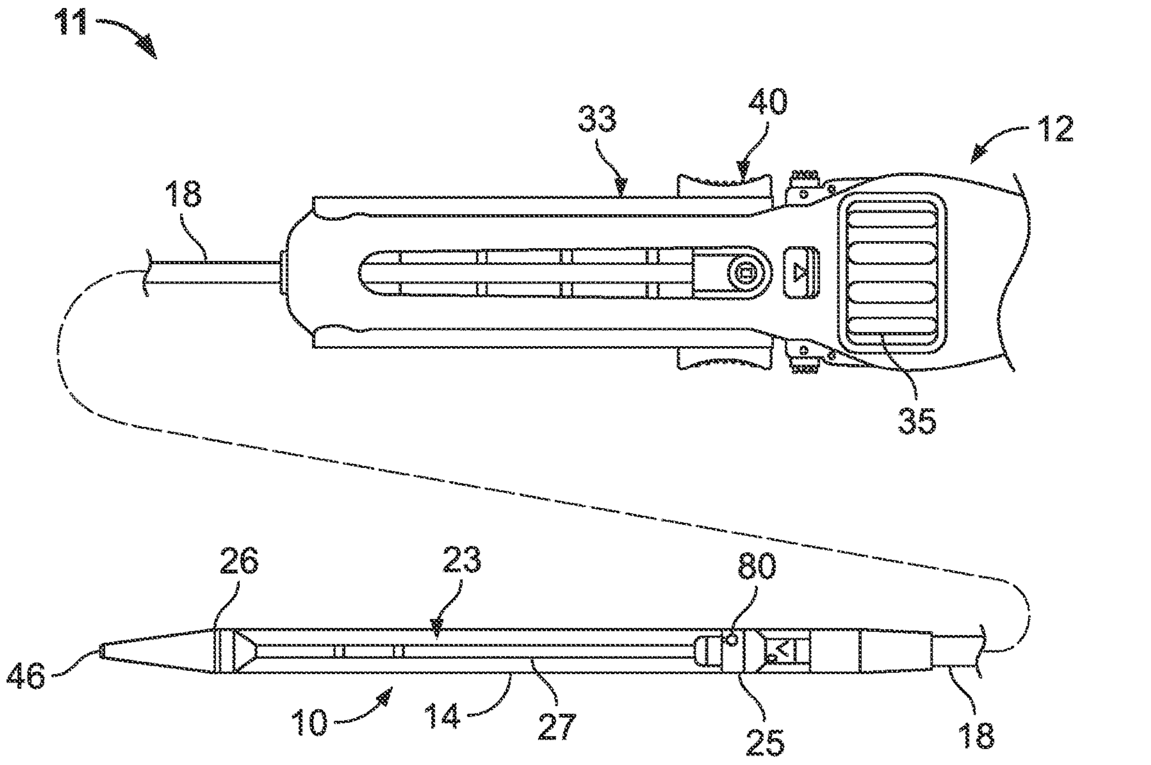
FIG. 1A is a top plan view of a portion of an operating handle for a delivery device, shown with a partial longitudinal cross-section of the distal portion of a transfemoral catheter assembly.
Figure 1B:
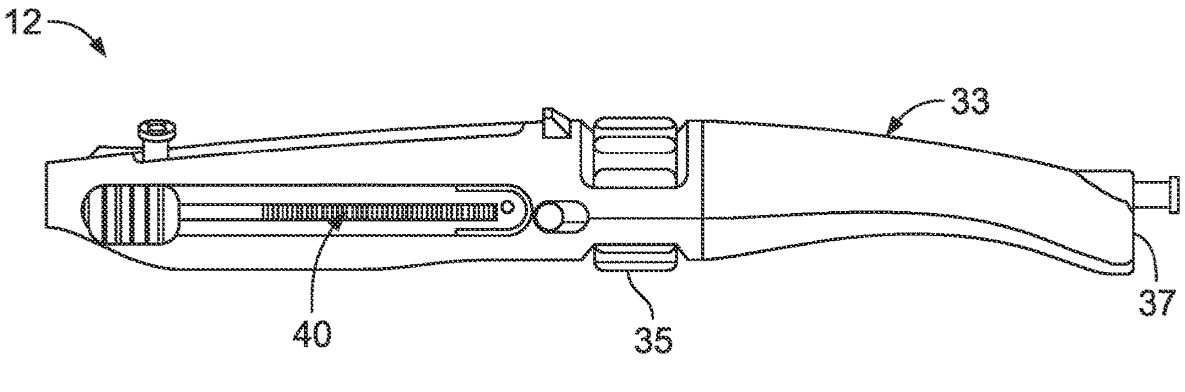
FIG. 1B is a side view of the handle of FIG. 1A.

FIGS. 1A-1B show a prosthetic heart valve delivery device 11. Generally, delivery device 11 includes an operating handle 12 coupled to an outer catheter shaft 18. The delivery device 11 may also include a distal sheath 14 for holding a prosthetic heart valve therein. Delivery device 11 includes catheter assembly 10 for delivering the heart valve to, and deploying the heart valve at, a target location, and operating handle 12 for controlling deployment of the valve from the catheter assembly. Delivery device 11 extends from proximal end 37 (FIG. 1B) to nosecone 46, which provides an atraumatic tip, at the distal end of catheter assembly 10. Catheter assembly 10 is adapted to receive a collapsible prosthetic heart valve (not shown) in compartment 23 defined around inner shaft 27 and covered by distal sheath 14.

Inner shaft 27 may extend through operating handle 12 to atraumatic tip 46 of delivery device 11, and may include retainer 25 affixed thereto at a spaced distance from nosecone 46 and adapted to hold a collapsible prosthetic valve in compartment 23. Retainer 25 may have recesses 80 therein that are adapted to hold corresponding retention members of the valve.

Distal sheath 14 surrounds inner shaft 27 and is slidable relative to inner shaft 27 such that it can selectively cover or uncover compartment 23. Distal sheath 14 is affixed at its proximal end to outer shaft 18, the proximal end of which is connected to operating handle 12. The distal end 26 of distal sheath 14 abuts nosecone 46 when the distal sheath is fully covering the compartment 23 and is spaced apart from the atraumatic tip when compartment 23 is at least partially uncovered.

Operating handle 12 is adapted to control deployment of a prosthetic valve located in compartment 23 by permitting a user to selectively slide outer shaft 18 proximally or distally relative to inner shaft 27, thereby respectively uncovering or covering compartment 23 with distal sheath 14. The proximal end of inner shaft 27 may be connected in a substantially fixed relationship to outer housing 33 of operating handle 12, and the proximal end of outer shaft 18 may be affixed to carriage assembly 40 that is slidable along a longitudinal axis of the handle housing, such that a user can selectively slide outer shaft 18 relative to inner shaft 27 by sliding carriage assembly 40 relative to the handle housing. For example, a user may rotate deployment actuator 35 to move carriage assembly 40 proximally, thus moving outer shaft 18 and distal sheath 14 proximally to uncover a prosthetic heart valve positioned within compartment 23 in the collapsed condition. As distal sheath 14 begins to clear the prosthetic heart valve, the prosthetic heart valve begins to expand to an expanded condition so that it may be fixed within the native heart valve annulus of interest.

Delivery device 11 may include a guidewire lumen (not illustrated) passing partially or entirely therethrough. The guidewire lumen may extend to distal tip 46. Prior to advancing delivery device 11 into the patient, a guidewire may be advanced to the site of implantation to aid in guiding the delivery device 11 to the desired site of implantation. In a TAVR procedure, the guidewire may be advanced into the left ventricle. Once the guidewire is positioned in the left ventricle, the distal tip 46 of delivery system 11 may be threaded over a proximal end of the guidewire, with the guidewire guiding the distal end of the delivery device 11 toward the left ventricle during advancement of the delivery system 11.

Figure 2A:
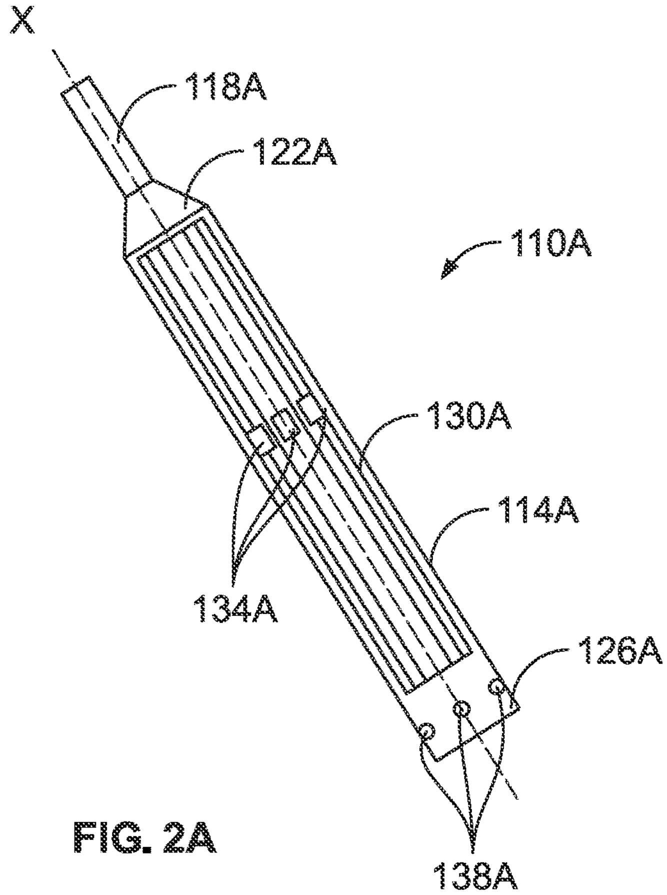
FIGS. 2A-2E are schematic side views of a distal portion of catheter assemblies according to various arrangements of a first aspect of the present disclosure.

FIG. 2A illustrates a catheter assembly 110A of a delivery system according to an arrangement of the present disclosure, with a nosecone providing a distal tip of the catheter assembly not illustrated for clarity. Catheter assembly 110A includes a sheath 114A extending longitudinally along a central axis X. Sheath 114A of the illustrated example is a cylinder centered on the central axis X, but in alternative arrangements sheath 114A may have other shapes and achieve a similar function. Sheaths in alternative arrangements may, for example, follow a curved centerline instead of a straight axis as illustrated. Moreover, sheaths in any arrangement described herein may be flexible, meaning the central axis X in any arrangement may become a curved centerline during use of the system. References to central axis X throughout the present disclosure should therefore be understood to disclose like features relative to a curved centerline, such as "axial locations" referring as well to positions along the curved centerline, and "radial distances" referring as well to distances perpendicular to a tangent line at a given point on the curved centerline.

A shaft 118A of the delivery system connects to a proximal end of sheath 114A at a hub 122A. A distal opening 126A is located at a distal end of sheath 114A opposite from hub 122A.

A prosthetic valve 130A in a collapsed configuration is disposed within sheath 114A. Prosthetic valve 130A includes commissure attachment features 134A. Commissure attachment features 134A of some known prosthetic valves 130A may be radioscopically visible, but typically have enough radiolucency to be difficult to see clearly within a patient. Further, retention of prosthetic valve 130A in a crimped shape can obscure the precise angular locations of commissure attachment features 134A.

Radioscopic markers 138A may be embedded within the material forming sheath 114A at a location between distal opening 126A and a distal end of prosthetic valve 130A. Radioscopic markers 138A may be spherical, semi-spherical, or disc shaped to provide the circular appearance illustrated in FIG. 2A. Though not illustrated in FIG. 2A, the delivery system includes an atraumatic nosecone, described further in various arrangements below, insertable to a certain depth into distal opening 126A. The nosecone closes distal opening 126A and prevents damage to tissue as the delivery system is advanced to the target site in a patient. Markers 138A may be embedded within sheath 114A at a distance from distal end 126A that is less than the depth to which the atraumatic nosecone may be inserted into the distal end of the sheath. The integration of markers 138A at respective locations distal of the distal end of prosthetic valve 130A in its pre-deployment location prevents the markers from being obscured within a radioscopic image from any perspective generally perpendicular to central axis X by the complex and overlapping structures of the prosthetic valve.

Markers 138A are easily identifiable within a radioscopic image of sheath 114A within a patient because markers 138A have a significant contrast in radiopacity from the material of sheath 114A. The contrast in radiopacity between markers 138A and nearby portions of sheath 114A may be a result of the relatively high or relatively low radiopacity of the markers. Markers 138A may, for example, be composed of highly radiopaque materials such as gold, tantalum, platinum, iridium, barium, nitinol, tungsten, or any combination thereof, or any other materials known for use as radiopaque markers in medical devices, whereas adjacent portions of sheath 114A may be composed of relatively radiotransparent material, such as any of a variety of common polymers. Alternatively, sheath 114A may be composed of a moderately radiolucent material, or may include a band of such material circumferentially aligned with markers 138A, and the markers may be voids within such material. In any case, a contrast in radiopacity between markers 138A and adjacent portions of sheath 114A is significant enough to make the markers 138A readily visible in an intra-operative radioscopic image of the sheath.

Sheath 114A of the illustrated example includes three markers 138A integrated therewith. Thus, the number of markers 138A integrated within sheath 114A in this example is equal to the number of commissure attachment features 134A of prosthetic valve 130A. Markers 138A may be angularly aligned about central axis X with commissure attachment features 134A, and thus the commissures themselves, of prosthetic valve 130A. Markers 138A thereby provide a readily identifiable visual reference for the locations of commissure attachment features 134A when viewed radioscopically. The alignment of commissure attachment features 134A with markers 138A may be accomplished either by referencing the markers, or otherwise determining the rotational position of sheath 114A, while inserting prosthetic valve 130A into sheath 114A or by providing axially extending and angularly spaced interior aligning features within sheath 114A to guide the prosthetic valve, retainer 25, or inner shaft 27 into the sheath in a predetermined orientation, or by employing both of these techniques. Alternatively, the delivery system, and in some examples, catheter assembly 10 specifically, may be constructed in such a manner that hub 122A, sheath 114A, or the nosecone, or whichever element contains markers 138A, or any combination of the foregoing, is not rotatable about central axis X relative to retainer 25. Due to such construction, recesses 80, and by extension, commissure attachment features 134A and the prosthetic commissures themselves, will always be at a known angular location relative to markers 138A. Such construction may, for example, permanently angularly align markers 138A about central axis X with recesses 80, meaning commissure attachment features 134A, and the prosthetic commissures themselves will also be angularly aligned with the markers when prosthetic valve 130A is loaded within catheter assembly 110A. In such arrangements, catheter assembly 110A is constructed to only receive prosthetic valve 130A in one predetermined angular position about central axis X relative to markers 138A and any other element of the catheter assembly. No reference to markers 138A is necessary during loading of prosthetic valve 130A into sheath 114A in such arrangements. Alternatively, such constraining features may be absent, and sheath 114A may be rotated to align markers 138A relative to commissure attachment features 134A before or after prosthetic valve 130A is disposed within the sheath, or during such disposition.

In the illustrated arrangement, markers 138A are circumferentially aligned with one another about a point on central axis X, angularly equidistant from one another about central axis X, and equally radially offset from central axis X. Markers 138A have a contrast in radiopacity from the material of sheath 114A at their axial location. Each marker 138A therefore has a contrast in radiopacity from material forming a portion of sheath 114A at the same location along central axis X. This contrast enables identification of markers 138A within a radioscopic image.

Numerous variations to the arrangement of markers 138A illustrated in FIG. 2A and described above are possible. Markers 138A may differ in number and angular spacing according to the number and angular spacing of the commissure attachment features that an intended type of prosthetic valve includes. Markers 138A may also vary in number and angular spacing without regard to the number and spacing of the commissure attachment features in the prosthetic valve, as long as the markers are arranged in a manner that enables discernment of the orientation of sheath 114A about central axis X within a radioscopic image. Markers 138A may also differ from one another in their distance from the distal opening 126A of sheath 114A so as to differentiate, for example, which specific commissure attachment feature a given marker corresponds to. Moreover, markers 138A may vary in shape. For example, any one or any combination of markers 138A may be circular and disc-shaped, spherical, semi-spherical, square, cubic, rectangular, triangular, pyramidal, or irregular in shape. The foregoing examples are non-limiting, and it should be understood that markers 138A may be of any shape or may be presented in any combination of shapes. Similarly, unless otherwise noted, any of the markers described herein may have any of the shapes described above or may vary their positions relative to one another as described above.

FIGS. 2B-2E illustrate catheter assemblies of delivery systems according to various alternative arrangements. In such arrangements, like numerals correspond to like features (i.e., sheaths 114B, 114C, 114D, and 114E are generally similar to sheath 114A) except for certain differences specified below.

Figure 2B:
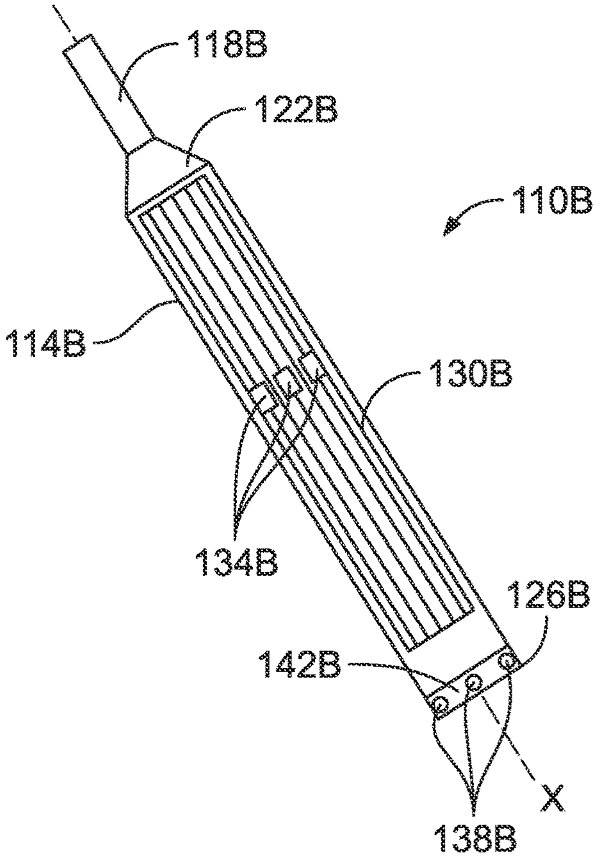

FIG. 2B illustrates a variant of the catheter assembly 110A of FIG. 2A. Catheter assembly 110B includes a shaft 118B connected to the proximal end of sheath 114B at a hub 122B. The distal end of sheath 114B includes a distal opening 126B. A prosthetic heart valve 130B having commissure attachment features 134B is disposed in a collapsed configuration within sheath 114B. As illustrated in FIG. 2B, markers 138B are integrated within a ring 142B located at the distal opening 126B of sheath 114B. Ring 142B serves to reinforce distal opening 126B such that the distal opening resists deformation from its resting shape. Ring 142B also aids engagement of a nosecone, discussed further below, within distal opening 126B.

Figure 2C:
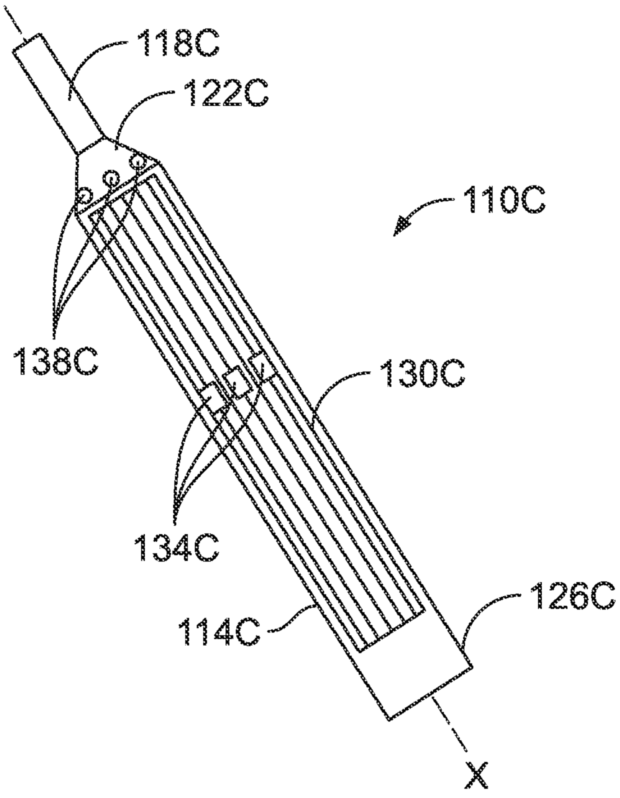

The catheter assembly 110C shown in FIG. 2C includes a shaft 118C connected to the proximal end of sheath 114C at a hub 122C. The distal end of sheath 114C includes a distal opening 126C. A prosthetic heart valve 130C having commissure attachment features 134C is disposed in a collapsed configuration within sheath 114C. Markers 138C shown in FIG. 2C, like markers 138A, may be spherical, semi-spherical, or disc shaped to create a circular appearance, or may be any of the other shapes described above. However, markers 138C are integrated into hub 122C instead of into sheath 114C. Markers 138C are thus axially offset from crimped prosthetic valve 130C, so the valve will generally not visually obscure the markers in radioscopy.

As a result of their relative positions in the catheter assembly, markers 138B and 138C also avoid becoming obscured by features of their respective prosthetic valves 130B and 130C.

Figure 2D:
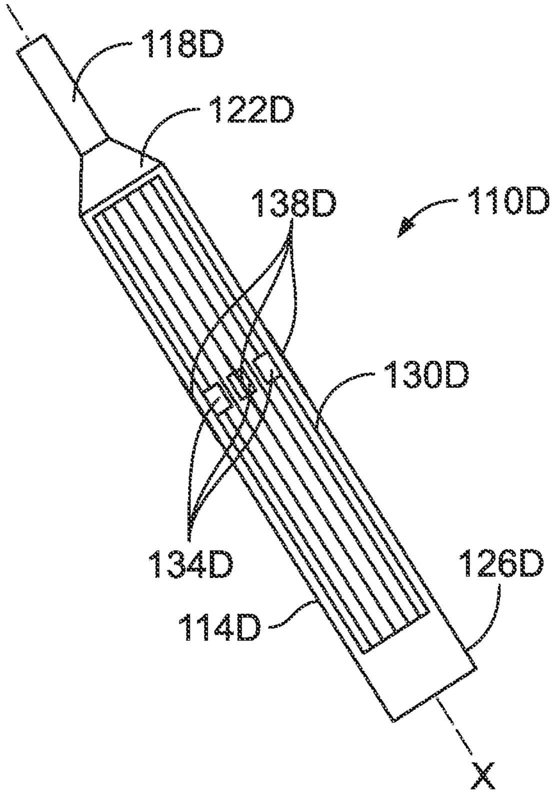

The catheter assembly 110D shown in FIG. 2D includes a shaft 118D connected to the proximal end of sheath 114D at a hub 122D. The distal end of sheath 114D includes a distal opening 126D. A prosthetic heart valve 130D having commissure attachment features 134D is disposed in a collapsed configuration within sheath 114D. Markers 138D, illustrated in FIG. 2D, are in the shape of straight lines positioned at locations on sheath 114D that overlie commissure attachment features 134D. Markers 138D cooperate with the partial radiopacity of commissure attachment features 134D to increase the visibility of the locations of the commissure attachment features within sheath 114D. Because markers 138D are axially extending lines, their precise angular locations may be easier to discern than those of the commissure attachment features 134D of the crimped valve.

Figure 2E:
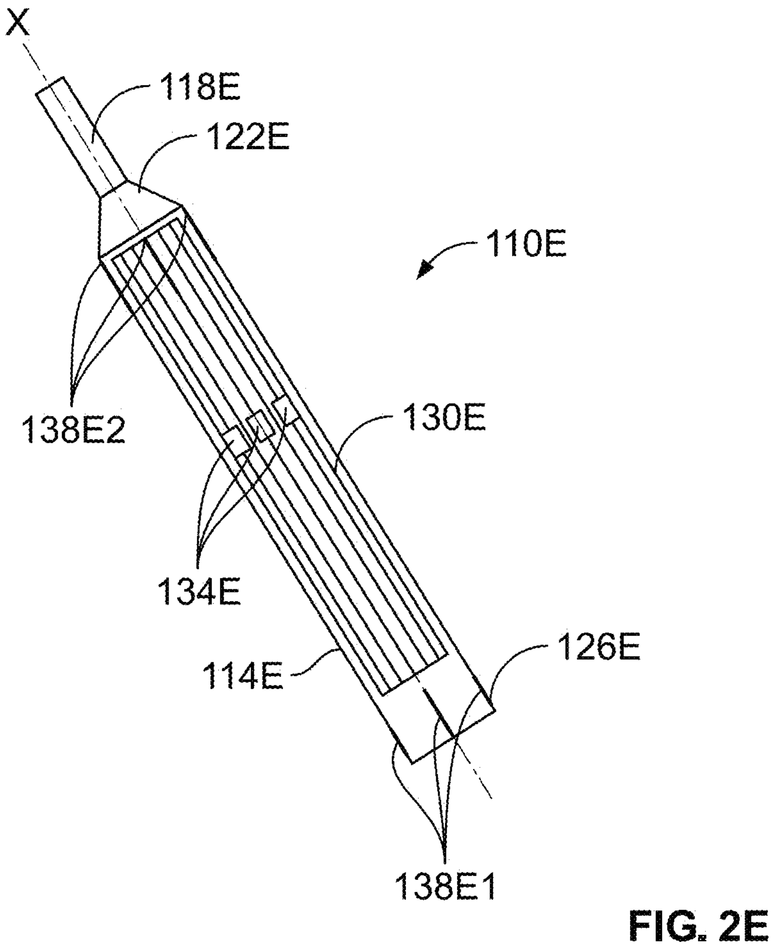

Turning to FIG. 2E, catheter assembly 110E includes a shaft 118E connected to the proximal end of sheath 114E at a hub 122E. A prosthetic heart valve 130E having commissure attachment features 134E is disposed in a collapsed configuration within sheath 114E. As shown in FIG. 2E, the markers exist in two groups of three, with a first group 138E1 near distal opening 126E of sheath 114E and a second group 138E2 near the proximal end of sheath 114E. Markers 138E1, like markers 138A, are separated from distal opening 126E by a distance that is less than the depth to which the distal nosecone is insertable into the distal opening. Markers 138E2 are also separated from hub 122E and the proximal end of sheath 114E by a similar distance. More particularly, markers 138E2 may be separated from the proximal end of sheath 114E by a distance equal to the distance separating markers 138E1 from distal opening 126E. Markers 138E1 and 138E2 collectively assist in providing quick reference to radioscopic images of sheath 114E by their presence at multiple axial locations along the sheath. Moreover, if either group of markers 138E1 and 138E2 is obscured, such as by a structure of the patient's anatomy, the other group may remain visible.

Markers 138B, 138C, 138D, and 138E1 and 138E2 may be made of the same materials, and may be modified, rearranged, or have differing shapes in any of the ways described above with regard to markers 138A. Generally, the arrangements of FIGS. 2B-2E may be varied or reconfigured in any of the ways described above with regard to FIG. 2A or with regard to any alternative arrangements thereof.

Figure 3:
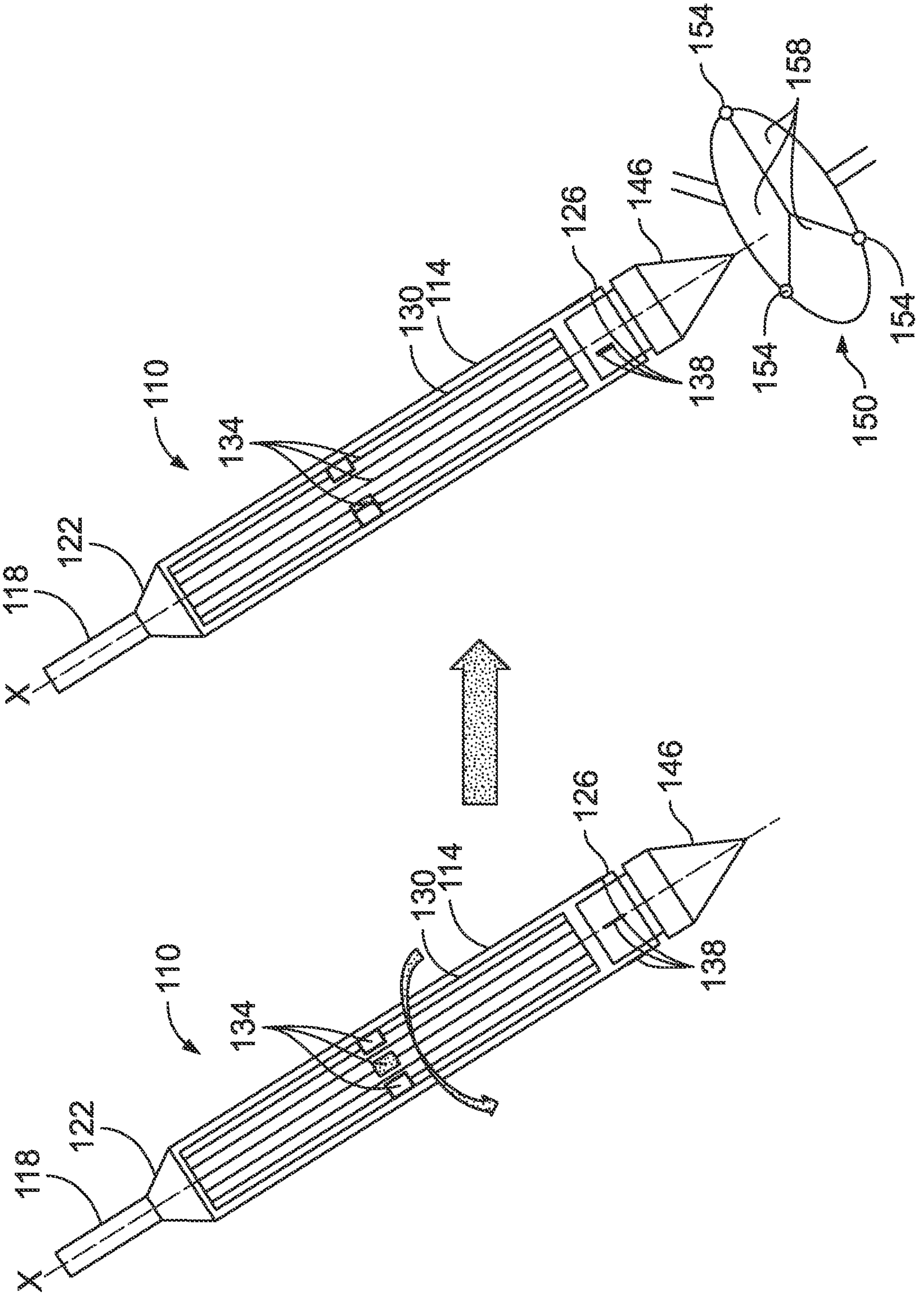
FIG. 3 is a schematic representation of steps in a process according to the present disclosure.

FIG. 3 illustrates stages within a process for using a catheter assembly according to any of the arrangements of the present disclosure. In FIG. 3, like numerals correspond generically to any like features elsewhere in the present disclosure (i.e., sheath 114 refers generically to sheaths 114A-114E described above, and nosecone 146 refers generically to the nosecone referred to above, or any of nosecones 246A-246E described below). "Catheter assembly," as used herein, refers to a structure at the distal end of a prosthetic valve delivery system that retains a prosthetic valve 130 as it is advanced to a target site within a patient, prior to its deployment. In the illustrated example, the catheter assembly 110 includes hub 122, sheath 114, and nosecone 146, though catheter assemblies in other arrangements may lack either or both of the hub and nosecone.

As shown in FIG. 3, a process of positioning the catheter assembly 110 of the delivery system within a patient's native valve 150 includes rotating the catheter assembly about central axis X to angularly align commissure attachment features 134, and thus the commissures of the prosthetic valve 130 themselves, with native commissures 154 of the native valve, which exist at the meeting point between adjacent native leaflets 158, and aligning the central axis X of the catheter assembly with the center of the native valve. The angular alignment may be achieved by rotating catheter assembly 110 until markers 138 are aligned with native commissures 154. If it is unclear whether a given marker 138 is on a near or far side of the catheter assembly as viewed radioscopically, an observer may note which direction that marker travels when the catheter assembly is rotated. Consideration of the direction of travel of a particular marker 138 relative to the direction of rotation of the catheter assembly will reveal whether that marker is on the near or far side of the catheter assembly. The process may further include rotating the catheter assembly in the opposite direction after determining the location of a marker 138 by observing that marker's direction of travel.

Since markers 138 are aligned with the commissure attachment features 134 of prosthetic heart valve 130 held within catheter assembly 110, once the markers are aligned with native commissures 154, the commissure attachment features of the prosthetic valve will also be aligned with the native commissures. In the illustrated arrangement, such alignment is reached when markers 138 are angularly aligned with native commissures 154. In other arrangements, markers 138 may be located elsewhere such that angular alignment between commissure attachment features 134 and native commissures 154 will result when there is angular alignment between one or more of the markers with other elements, such as, for example, native anatomic features of the patient other than native commissures 154. Prosthetic valve 130 may be deployed after commissure attachment features 134 have been aligned with native commissures 154, and the central axis X of the catheter assembly has been aligned with the center of native valve 150.

As shown above in FIGS. 2A-2E and 3, the catheter assembly may be radioscopically marked by integration of markers within hub 122 or sheath 114, or both the hub and sheath. Turning to FIGS. 4A-4E, the catheter assembly may be marked, alternatively or additionally, by integrating markers within the nosecone.

Figure 4A:
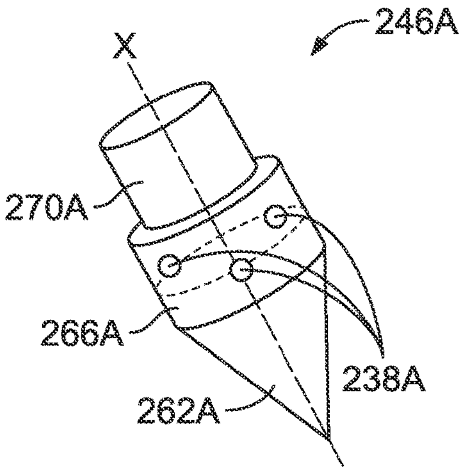
FIGS. 4A-4E are oblique perspective views of nosecones according to various arrangements of a second aspect of the present disclosure.

Illustrated in FIG. 4A is a nosecone 246A generally alike in shape and structure to nosecone 146 of FIG. 3. In the illustrated example, nosecone 246A has a tip 262A in the shape of a cone, a cylindrical barrel 266A at the proximal end of the tip, and a plug 270A extending proximally from the barrel, but with a smaller diameter. Plug 270A is shaped and dimensioned to closely fit within the distal opening 126 of sheath 114. Barrel 266A has a diameter that is greater than the inner diameter of distal opening 126, thereby preventing its insertion therein. As a result, the depth to which nosecone 246A can be inserted into sheath 114 is limited. As noted, in the illustrated example, tip 262A is conical, and barrel 266A is cylindrical and roughly equal in diameter to the outer diameter of sheath 114. Such shape of tip 262A and shape and size of barrel 266A facilitate atraumatic travel of the catheter assembly through a patient. However, in other examples, tip 262A may have a different shape, such as a more truncated conical shape or a more rounded tip, and barrel 266A may have a different size and shape.

Nosecone 246A includes three markers 238A. Though markers 238A have a circular appearance in the illustrated example, they may be generally alike in every respect to markers 138 according to any of the examples discussed above, except that markers 238A are embedded within the barrel 266A of nosecone 246A. Therefore, markers 238A each have a contrasting radiopacity to the material of nosecone 246A, at least in the portion of nosecone 246A at the same axial location and distance from the central axis X of the nosecone. FIG. 4A shows the markers as if nosecone 246A is transparent. That is, from the point of view of the viewer, one marker is on the near side of the nosecone and two markers are on the far side of the nosecone.

In the illustrated example, a ring of smaller radioscopically visible elements is provided within nosecone 246A at the same axial location as markers 238A, though such additional smaller elements may be omitted from other arrangements.

FIGS. 4B-4E illustrate nosecones according to various alternative arrangements. In such arrangements, like numerals correspond to like features (i.e., nosecones 246B, 246C, 246D, and 246E are generally similar to nosecone 246A) except for certain differences specified below. Thus, nosecone 246B has a tip 262B, a cylindrical barrel 266B at the proximal end of the tip, and a plug 270B extending proximally from the barrel; nosecone 246C has a tip 262C, a cylindrical barrel 266C at the proximal end of the tip, and a plug 270C extending proximally from the barrel; nosecone 246D has a tip 262D, a cylindrical barrel 266D at the proximal end of the tip, and a plug 270D extending proximally from the barrel; and nosecone 246E has a tip 262E, a cylindrical barrel 266E at the proximal end of the tip, and a plug 270E extending proximally from the barrel. Like FIG. 4A, FIGS. 4B-4E show the markers as if nosecones 246B, 246C, 246D, and 246E are transparent. Thus, markers on the opposite side of each nosecone from the perspective of the figures are made visible through the nosecone.

Figure 4B:
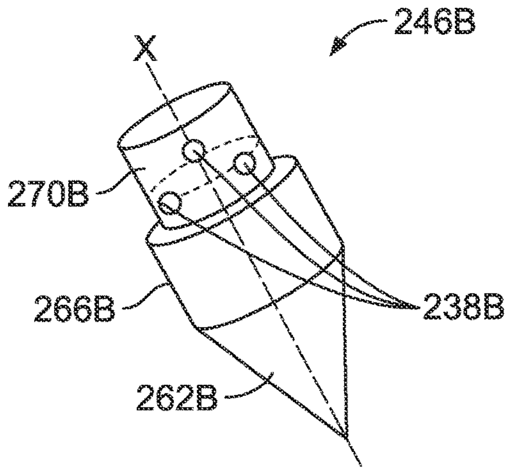
Figure 4C:
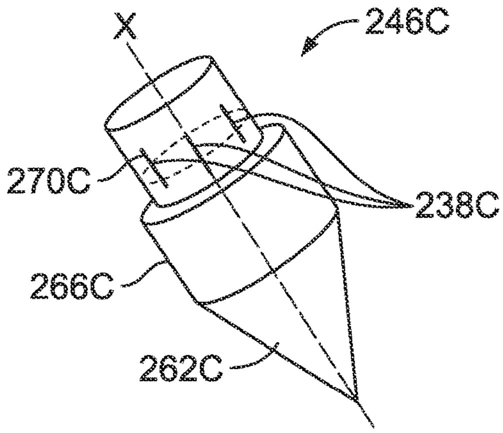

Markers 238B of FIG. 4B are embedded in the plug 270B instead of the barrel 266B of nosecone 246B and are offset from central axis X by a smaller distance, but are otherwise generally similar to markers 238A. Markers 238C of FIG. 4C are located within plug 270C of nosecone 246C, similarly to markers 238B, but have the shape of axially extending straight lines. Though not illustrated, markers having the same shape and/or the same radial offset as markers 238C may be located elsewhere within any nosecone 246, such as within the barrel 266. In still further arrangements, markers having any of the shapes described above may be located within the tip 262, barrel 266 or plug 270 of any nosecone 246.

Figure 4D:
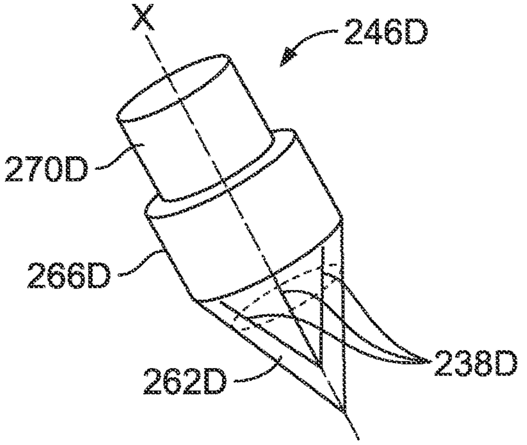

FIG. 4D illustrates a nosecone 246D having markers 238D in the form of linear branches embedded beneath an outer surface of tip 262D and extending proximally from a convergence point. In the illustrated example, the convergence point between markers 238D is centered on the central axis X of nosecone 246D and located near the distal extreme of tip 262D. Each marker 238D extends away from the convergence point along a vector having both an axial component and a radial component, enabling the markers to be individually visible when viewed radioscopically from a perspective that is orthogonal to central axis X. In the illustrated example, the markers 238D extend along vectors having radial components that extend at equal angles relative to one another, though in other examples the angles between different markers 238D may vary. In other alternatives, markers 238D may each include purely radially extending segments or purely axially extending components. The convergence point may also be located off the central axis X or within barrel 266D or plug 270D in alternative arrangements, and in further arrangements, the branches forming markers 238D may extend distally from the convergence point.

Figure 4E:
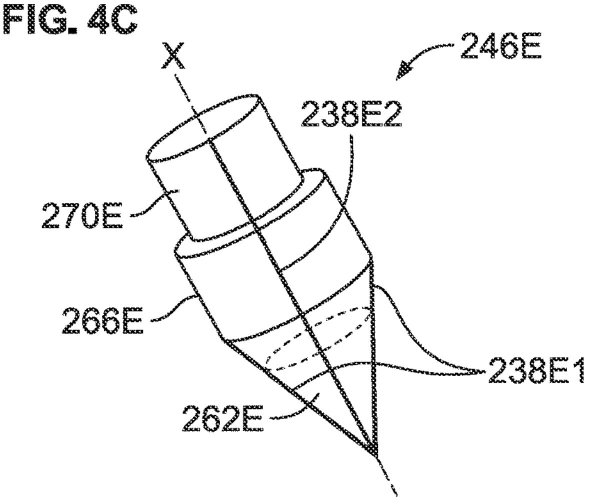

FIG. 4E illustrates a nosecone 246E having markers 238E1 and 238E2 that are also in the form of branches extending proximally from a convergence point. While markers 238D are entirely beneath an exterior surface of nosecone 246D, markers 238E1 run along the exterior surface of nosecone 246E and converge at a distalmost point of tip 262E. Accordingly, each of markers 238E1 extends away from the convergence point along a respective vector that includes an axial component and a radial component. Markers 238E1 only extend along tip 262E and terminate at a distal end of barrel 266E. Marker 238E2 extends along central axis X along the entire axial length of nosecone 246E. Marker 238E2 may, for example, extend directly along the central axis X, or may encircle a lumen within nosecone 246E that extends along the central axis.

Markers 238A-238E may be made of any of the materials, and may be modified or rearranged, and may vary in shape in any of the ways described above with regard to markers 138A-138E, except that markers 238A-238E are located within a respective nosecone 246A-246E.

All of the figures in the accompanying drawings and the associated description are generally consistent with systems and methods for TAVR. However, the methods and structures disclosed herein can readily be adapted for replacement of any other valve within a patient.

Returning to the generic numbering introduced above for description of FIG. 3, and referring generally to any of the examples illustrated in FIGS. 2A-4E, a common feature of each arrangement illustrated in the accompanying drawings is the inclusion of markers 138 in a group of three, with the markers within the group being circumferentially aligned, offset from the central axis X of the catheter assembly 110 by an equal distance, and angularly equidistant from one another about central axis X. The catheter assembly 110 of each arrangement illustrated in the drawings is therefore radioscopically marked in a pattern having discrete rotational symmetry of the third order about central axis X. Thus, for any one radioscopic image of the markers 138 of any catheter assembly 110 described herein that can be projected onto a plane along which central axis X lies, there exist five other unique planes along which the central axis X lies onto which an identical radioscopic image of the markers could be projected. If the catheter assembly 110 as a whole is also symmetrical about central axis X, there would be an identical radioscopic image of the entire catheter assembly 110 projected on each of the six aforementioned planes. Thus, by reference to markers 138 within any still radioscopic image of the catheter assembly 110 on a viewing plane parallel to central axis X, an observer will be able to narrow down the rotational position of the sheath 114 to six possibilities. For example, where three identical, symmetrical, and angularly evenly angularly spaced markers 138 are used and shown in a radiographic image, an observer may not be able to differentiate any one marker from another, or to determine if any one marker is on a side of the catheter nearer to or further from the perspective of the radiographic image. Similarly, if catheter assembly 110 is flexed or curved, and therefore extends along a curved centerline, an observer viewing the catheter assembly from a perspective that is orthogonal to the centerline at a point centered among the markers 138 will be able to narrow down the rotational position of the sheath 114 to six possibilities.

The number of rotational positions of sheath 114 about the central axis X of the catheter assembly that produce an identical image of markers 138 to an observer viewing a still radioscopic image of the sheath is directly proportional to the order of rotational symmetry of the markers about the central axis. This number of identical images can therefore be reduced by introducing asymmetries to the positions and/or shapes of markers 138. Uneven angular spacing, differing axial locations, differing shapes, or any other differences introduced to make some markers 138 distinguishable from others would reduce the number of times the same image can be produced as sheath 114 is rotated. Circumferential asymmetry in the shape of any or all markers 138 themselves would clarify the rotational position of sheath 114 by enabling an observer to determine, from a single radioscopic image, whether the asymmetrical marker is on the near or far side of the sheath 114. Any of the foregoing asymmetries may therefore be introduced to any of the various arrangements of capsule assemblies described herein.

To summarize the foregoing, disclosed is a prosthetic valve delivery system including a catheter assembly having a central axis and being adapted to retain a prosthetic valve in a collapsed state, and a marker integrated with the catheter assembly at a marker location radially offset from the central axis; and the marker may have a contrasting radiopacity to the radiopacity of a material of the catheter assembly circumferentially aligned with the marker location; and/or the catheter assembly may comprise a sheath and a distal nosecone; and/or the catheter assembly may be integrated within a reinforcing ring at a distal opening of the sheath in which the distal nosecone is received; and/or the marker may be integrated within the distal nosecone; and/or the marker may include a plurality of branches each extending from a shared convergence point along a respective vector that includes an axial component defined relative to the central axis; and/or the marker may be a first marker, the marker location is a first marker location. The system may further comprise an additional marker integrated with the catheter assembly at an additional marker location; and the additional marker may have a contrasting radiopacity to a material of the catheter assembly circumferentially aligned with the additional marker location; and/or the additional marker location may be circumferentially aligned with the first marker location; and/or the first marker location and the additional marker locations may be offset from the central axis by equal distances; and/or the first marker location and the additional marker locations may be angularly equidistant from one another about the central axis; and/or the catheter assembly may be constructed to only be able to receive the prosthetic valve in a predetermined angular position about the central axis within the catheter assembly, and the predetermined angular location position may be wherein each of the first marker location and the additional marker location are angularly aligned with commissure attachment features of the prosthetic valve; and/or wherein the system may include two additional markers; and/or the catheter assembly may comprise a sheath, the sheath having a proximal end and a distal end, and the nosecone extending into the distal end of the sheath by a depth. The first marker location may be separated axially relative to the central axis X from the distal end of the sheath by a distance less than the depth. The additional marker location may be separated axially relative to the central axis X from the proximal end of the sheath by a distance less than the depth; and/or the marker may be a void in a radiopaque component; and/or the marker may be a component constructed from radiopaque material; and/or the marker may be formed from a material selected from the group consisting of gold, tantalum, iridium, nitinol, platinum, barium, tungsten and combinations thereof; and/or the marker may have an elongate, linear shape; and/or the catheter assembly may be constructed to only be able to receive the prosthetic valve in a predetermined angular position about the central axis within the catheter assembly and the marker is angularly located relative to the central axis such that the prosthetic valve would be at an intended angular position for delivery if the prosthetic valve were received in the catheter assembly and the sheath were located in a human heart and the marker were angularly aligned relative to the central axis with a predetermined anatomical feature of the heart;

the marker may have a circular shape; and/or the marker may have a spherical shape.

Also disclosed is a method of delivering a prosthetic valve into a patient using the system according to any of the foregoing arrangements may comprise making visual reference to the marker within a radioscopic image of the patient while rotating the catheter assembly to a delivery orientation in which the marker is angularly aligned with a commissure of the native valve and while the prosthetic valve is disposed within the catheter assembly such that a commissure attachment feature of the prosthetic valve is angularly aligned with the marker relative to the central axis; and deploying the prosthetic valve while the catheter assembly is in the delivery orientation; and/or making visual reference to the marker may include determining which side of the catheter assembly includes the marker location by observing a direction in which the marker travels within the image when the catheter assembly is rotated.

Also disclosed a prosthetic valve delivery system that may comprise a catheter assembly having a central axis and being adapted to retain a prosthetic valve in a collapsed state, the catheter assembly being radioscopically marked such that, for any radioscopic image of the catheter assembly obtained from a perspective orthogonal to the central axis, at most six unique rotational positions of the catheter assembly about the central axis are possible.

Also disclosed is a prosthetic valve delivery system that may comprise a catheter assembly having a central axis and being adapted to retain a prosthetic valve in a collapsed state. The system may also comprise a plurality of markers integrated with the catheter assembly at respective marker locations, each marker location being circumferentially aligned with and angularly equidistant from one another relative to the central axis, the markers having a contrasting radiopacity to a material of the catheter assembly circumferentially aligned with the marker location.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic valve delivery system, comprising:

a catheter assembly having a central axis and being adapted to retain a prosthetic valve in a collapsed state; and a plurality of markers integrated with the catheter assembly at a-marker locations radially offset from the central axis, each of the marker locations being offset from a next adjacent marker location by an angular distance about the central axis, each of the markers having a contrasting radiopacity to the radiopacity of a material of the catheter assembly circumferentially aligned with the marker locations, wherein each of the marker locations is positioned to be angularly aligned about the central axis with a respective commissure attachment feature of the prosthetic valve when the prosthetic valve is retained in the catheter assembly.

2. The system of claim 1, wherein the catheter assembly comprises a sheath and a distal nosecone.

3. The system of claim 2, wherein the plurality of markers are integrated within a reinforcing ring at a distal opening of the sheath in which the distal nosecone is received.

4. The system of claim 2, wherein the plurality of markers are integrated within the distal nosecone.

5. The system of claim 4, wherein the plurality of markers include a plurality of branches each extending from a shared convergence point along a respective vector that includes an axial component defined relative to the central axis.

6. The system of claim 1, wherein the marker locations are circumferentially aligned about the central axis.

7. The system of claim 1, wherein the marker locations are radially offset from the central axis by equal distances.

8. The system of claim 1, wherein the marker locations are angularly equidistant from one another about the central axis.

9. The system of claim 1, wherein the catheter assembly is constructed to be able to receive the prosthetic valve therein only in a predetermined angular position about the central axis, the predetermined angular position being that in which each of the marker locations is angularly aligned with a respective one of the commissure attachment features of the prosthetic valve.

10. The system of claim 1, wherein:

the catheter assembly comprises a sheath having a proximal end and a distal end, and a nosecone extending into the distal end of the sheath by a depth;

a first one of the marker locations is separated axially relative to the central axis from the distal end of the sheath by a distance less than the depth; and another one of the marker locations is separated axially relative to the central axis from the proximal end of the sheath by a distance less than the depth.

11. The system of claim 1, wherein each of the markers is a void in a radiopaque component.

12. The system of claim 1, wherein each of the markers is a component that is constructed from radiopaque material.

13. The system of claim 1, wherein each of the markers is formed from a material selected from the group consisting of gold, tantalum, iridium, nitinol, platinum, barium, tungsten and any combinations thereof.

14. The system of claim 1, wherein the catheter assembly is constructed to be able to receive the prosthetic valve only in a predetermined angular position about the central axis within the catheter assembly and each of the markers is angularly located relative to the central axis such that the prosthetic valve will be at an intended angular position for delivery when the prosthetic valve is received in the catheter assembly and the sheath is located in a human heart with at least one of the markers angularly aligned relative to the central axis with a predetermined anatomical feature of the heart.

15. A method of delivering a prosthetic valve into a patient using the system of claim 1, comprising:

when the prosthetic valve is retained in the catheter assembly, ensuring that each of the marker locations is angularly aligned with respect to the central axis with a respective commissure attachment feature of the prosthetic valve;

making visual reference to the plurality of markers within a radioscopic image of the patient while rotating the catheter assembly to a delivery orientation in which each of the plurality of markers is angularly aligned with a respective commissure of the native valve; and deploying the prosthetic valve while the catheter assembly is in the delivery orientation.

16. The method of claim 15, wherein making visual reference to the plurality of markers includes determining which side of the catheter assembly includes the marker locations by observing a direction in which each of the markers travels within the image when the catheter assembly is rotated.

* * * * *